United States Patent [19]

Johnston

[11] 4,179,453

[45] Dec. 18, 1979

[54] PROCESS FOR PREPARING 17β-CARBOXY-5-ANDROSTEN-3-ONES

[75] Inventor: David B. R. Johnston, Warren, N.J.

[73] Assignee: Merck & Co., Inc., Rahway, N.J.

[21] Appl. No.: 896,120

[22] Filed: Apr. 13, 1978

[51] Int. Cl.$^2$ .............................................. C07J 9/00
[52] U.S. Cl. ................................ 260/397.1; 260/239.5
[58] Field of Search ...................................... 260/397.1

[56] References Cited

PUBLICATIONS

King et al., "J. Am. Chem. Soc.", vol. 66, (1944), p. 1612.
"Organic Reactions in Steroid Chemistry", by Fried et al., p. 148.

*Primary Examiner*—Elbert L. Roberts
*Attorney, Agent, or Firm*—Raymond M. Speer; Mario A. Monaco

[57] ABSTRACT

A process for preparing 17β-carboxy-4-androsten-3-ones comprising the steps of (1) reacting a 17β-(1-ketoethyl)-5-androsten-3-ol, for example, pregnenolone, with pyridine and iodine to form a pyridinium iodide compound; (2) reacting the pyridinium iodide compound with alkali metal methoxide in methanol to form a methyl-5-androsten-3-ol-17β carboxylate; (3) oxidizing the product of Step (2) preferably with aluminum isopropoxide to form methyl-4-androsten-3-one-17β-carboxylate; and (4) hydrolyzing the product of Step (3) to the corresponding 17β-carboxylic acid, salt, or ester. The 17β-carboxy-4-androsten-3-ones are useful as intermediates for preparation of N-substituted-17β-carbamoylandrost-4-en-3-one and 4-aza-17β-substituted-5α-androstan-3-one 5α reductase inhibitors.

4 Claims, No Drawings

PROCESS FOR PREPARING 17β-CARBOXY-5-ANDROSTEN-3-ONES

BACKGROUND OF THE INVENTION

1. Field of the Invention

The present invention is concerned with a process for preparing 17β-carboxy-4-androsten-3-ones.

2. Description of the Prior Art

Heretofore, 17β-carboxy-4-androsten-3-ones have been prepared from the corresponding 17β-(1-ketoethyl)-5-androsten-3-ols by means of the haloform reaction in which cleavage was brought about by addition of dilute sodium hydroxide to the starting material, followed by a slight excess of iodine in potassium iodide solution, warming, and addition of water. However, this reaction has been found to give poor yields and to require the use of expensive reagents. By contrast, the method of the present invention is characterized by rapid and high yield of product, and a more efficient use of expensive reagents.

It has also been known to prepare 3β-hydroxy-5-androstene-17-carboxylic acid by treating 3β-hydroxy-5-pregnene-20-one with iodine and pyridine and carrying out alkaline decomposition of the 21-pyridinium intermediate. See King, L. carroll, *J. Am. Chem. Soc.*, Vol. 66, p. 1612 (1944). However the method of the present invention permits preparation of the methyl carboxylate ester directly, rather than the acid which is formed in the King method. The ester is a blocking group which permits subsequent modifications to the A and B rings.

SUMMARY OF THE INVENTION

The method of the present invention is useful for preparing 17β-carboxy-4-androsten-3-one compounds of the following formula:

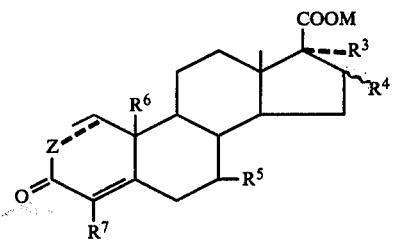

where $R^3$, $R^4$, $R^5$, and $R^6$, are the same or different and are hydrogen or lower alkyl; $R^7$ is hydrogen or cyano; M is hydrogen, lower alkyl, or alkali metal; and Z is CH—$R^9$ where $R^9$ is hydrogen, α-fluoro, or α-lower alkyl; and the dotted line between positions 1 and 2 represents the possibility of a single bond when Z is CH—$R^9$ and a double bond when Z is C—$R^9$.

The 17β-carboxy-4-androsten-3-one compounds are useful as starting materials and intermediates for preparation of N-substituted-17β-carbamoylandrost-4-en-3-one 5α reductase inhibitors described in copending application Ser. No. 896,119, filed Apr. 13, 1978. They are also useful as starting materials and intermediates for preparation of 4-aza-17β-substituted-5α-androstan-3-one 5α reductase inhibitors described in copending application Ser. No. 896,118, filed Apr. 13, 1978. The 5α reductase inhibitors are useful in treating the hyperandrogenic conditions of acne vulgaris, seborrhea, male pattern baldness and female hirsutism by topical administration, and of benign prostatic hypertrophy by parenteral administration.

The method of the present invention may be illustrated by the following reaction scheme:

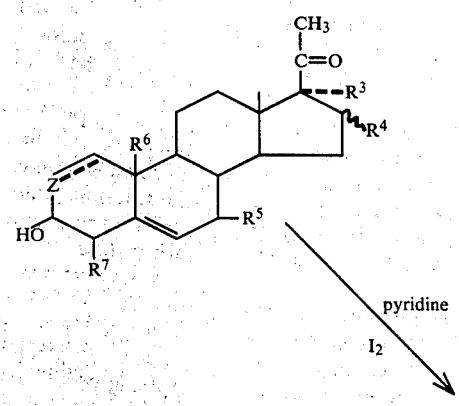

-continued

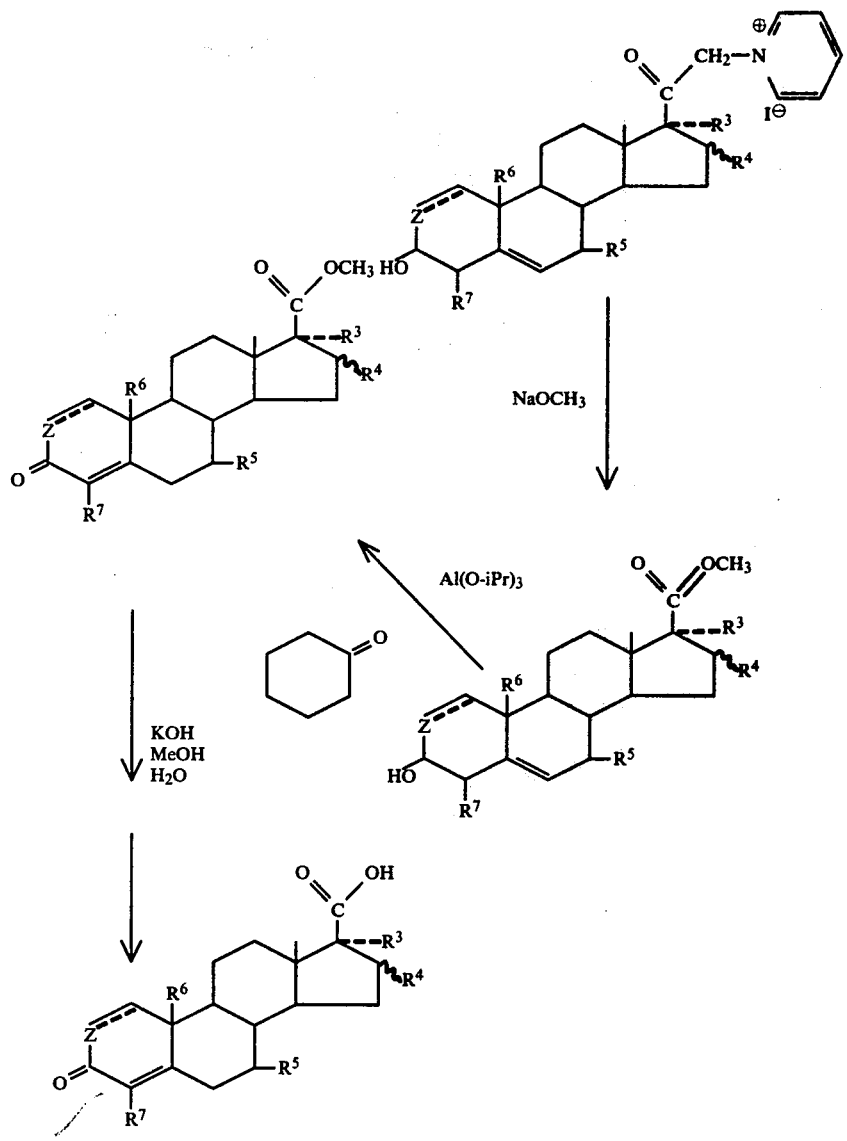

The first step of the method of the present invention comprises reacting a 17β-(1-ketoethyl)-5-adrosten-3-ol, i.e., a pregnenolone or 19-nor pregnenolone, with pyridine and iodine to form a pyridinium iodide compound. Approximately two moles of pyridine per mole of the androstenol compound are required, together with approximately one mole of iodine. Slight molar excesses should ordinarily be employed. Crushed iodine is utilized in order to avoid large pieces of iodine which might require extended stirring to dissolve, which in turn might possibly initiate premature crystallization. The reaction is slightly exothermal and it is carried out at 80° C. to reflux of pyridine, preferably at 100° C., at ambient pressures, and for a period of from about 1.5 to 2 hours. Repeated washing of the product with pyridine is required in order to remove the bulk of contaminating pyridinium hydroiodide which is formed, although small remaining amounts do not interfere with the subsequent step.

In the second step of the method of the present invention, the pyridinium iodide compound prepared in the first step is reacted with an alkali metal methoxide, preferably sodium methoxide. The reaction is carried out in methanol solvent, at reflux temperature of the methanol and ambient pressures. The reaction forms a methyl-5-androsten-3-ol-17β-carboxylate.

In the third step of the method of the present invention, the carboxylate product of the second step is oxidized, preferably by means of the Oppenauer reaction utilizing aluminum isopropoxide or other alkoxide. The reaction is carried out in an anhydrous hydrocarbon solvent, preferably toluene. Cyclohexanone is employed as the hydrogen acceptor. The reaction is carried out at a temperature of from about 80° C. to reflux of toluene, preferably reflux, and for a period of from about 3 to 5 hours. A series of extractions, employing saturated Rochelle salt solution, saturated sodium chloride solution, water and ethyl acetate, are carried out to separate the product, a methyl 4-androsten-3-one-17β-carboxylate.

In the fourth step of the method of the present invention, the methyl ester product of the third step is converted to the corresponding acid or salt. The acid is prepared by alkaline hydrolysis of the ester, preferably utilizing potassium hydroxide in a mixture of methanol and water, at the reflux temperature of methanol. The acid is extracted with ethyl acetate and water under acid conditions. Where it is desired to prepare the alkali metal salt, the reaction mixture may simply be lypholyzed to dryness.

The following example will serve to illustrate the manner in which the method of the present invention may be carried out.

EXAMPLE

17β-carboxy-4-androsten-3-one

Step A. Preparation of (3β-hydroxypregn-5-en-20-one-21-yl) pyridinium iodide In a large beaker clamped in an oil bath maintained at 100° C. and containing 100 ml. of pyridine are placed 50 g. of pregnenolone. The beaker is capped with a watch glass and the mixture is stirred until solution is complete. To this mixture is added 43.3 g. of crushed iodine as quickly as possible, and the opaque black-brown solution is quickly stirred to fully dissolve the iodine as much as possible before obvious reaction, and in particular, crystallization begins. Within a few minutes a gentle but brisk reaction begins as indicated by bubbling. Heating is continued for about 1.5 to 2 hours. The reaction mixture is allowed to cool, and the granular reaction product is gently broken up with a spatula and transferred to a sintered glass funnel, crushed to a firm layer, and sucked dry. The beaker is rinsed with pyridine and added to the cake; the cake is resuspended, pressed to a layer again, and sucked dry again. One or two more washes are usually suffient to remove the bulk of contaminating pyridinium hydroiodide present. The cake is now sucked dry under a nitrogen atmosphere to give from 72 g. to 78 g. of the pyridinium iodide compound, having a m.p. of 223°–225° C. Theoretical yield is 83 g. The product is usually contaminated with pyridinium hydroiodide, but since this contaminant does not appear to interfere with the next step, no attempt is made to remove it.

Step B. Preparation of methyl 5-androsten-3β-ol-17β-carboxylate

The pyridinium iodide product from Step A above is refluxed for 1 hr. in 500 to 1000 ml. of methanol containing 25 to 50 g. of sodium methoxide. The reaction mixture is then cooled and poured into 5 l. of ice water. The product is then extracted with ethyl acetate several times, accompanied by water washing and drying. The product is separated and purified by recrystallization.

Step C. Preparation of methyl 4-androsten-3-one-17β-carboxylate

A solution of 36 g. of the ester product of Step B in 500 ml. of toluene and 150 ml. of distilled cyclohexanone, is dried by azeotropically distilling off about 50 ml. of solvent. The reaction solution is then treated with about 10 g. of aluminum isopropoxide in 50 ml. of dry toluene. The reaction mixture is stirred and heated, distilling off from 300 to 400 ml. of solvent over 3 to 4 hours. The remaining reaction mixture is cooled, extracted twice with 100 ml. of saturated Rochelle salt solution, twice with saturated sodium chloride solution, and once with water. A lumpy interface persists throughout and is separated with the last water wash into a separate flask. This phase is acidified with 7.5 N hydrochloric acid and extracted three times with ethyl acetate, each separate extract then in turn being extracted with the combined Rochelle salt and sodium chloride washes from above. The combined ethyl acetate extracts are added to the main organic phase, diluted with an equal volume of water and concentrated in vacuo until distillation effectively stops. The dilution and concentration is repeated several times. The residue is taken up in chloroform, dried, and concentrated to an oil. The oily residue is crystallized from hexane, and the resulting solid is washed with ether and petroleum ether, and finally recrystallized from methanol to give 26 g. of methyl 4-androsten-3-one-17β-carboxyate.

Step D. Preparation of 4-androsten-3-one-17β-carboylic acid

To a stirred solution of 10.123 g. of potassium hydroxide in a mixture of 11.3 ml. of water and 180 ml. of methanol, is added 15 g. of the methyl carboxylate ester product of Step C. above, which is rinsed in with 22.5 ml. of additional methanol. The reaction mixture is placed in an oil bath and heated to reflux, where it is maintained overnight under a nitrogen atmosphere. The reaction mixture is then removed from the heat, concentrated briefly under the nitrogen stream, and then poured into a mixture of 750 ml. of ethyl acetate and 750 ml. of ice water containing 75 ml. of 2.5 N hydrochloric acid. The reaction mixture is shaken well and the resulting layers are separated. The aqueous layer is extracted again with 750 ml. of ethyl acetate and the combined ethyl acetate extracts are washed with 400 ml. of a saturated sodium chloride solution. The combined extracts are dried, filtered, and concentrated. The product is recrystallized from ethyl acetate to yield 11.78 g., m.p. 255° C.

When used as intermediates for preparation of N-substituted-17β-carbamoylandrost-4-en-3-one and 4-aza-17β-substituted-5α-androstan-3-one 5α reductase inhibitors, the 17β-carboxy-4-androstan-3-ones prepared by the method of the present invention are usually converted to the acid chloride by the method of Wilds and Shunk, J. Am. Chem. Soc., 70, 2427 (1948). The alkali metal salts of the 17β-carboxy compounds are particularly useful in this regard.

Moreover, the lower alkyl 17β-carboxylates prepared by the method of the present invention have additional utility as intermediates for preparing N-substituted-17β-carbamoylandrost-4-en-3-one 5α reductase inhibitors directly by reaction with the appropriate amine.

What is claimed is:

1. A method for preparing a 17β-carboxy-4-androsten-3-one having the formula:

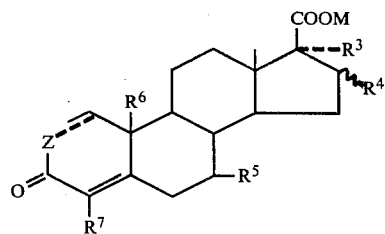

where
R$^3$, R$^4$, R$^5$, and R$^6$ are the same or different and are hydrogen or lower alkyl;
R$^7$ is hydrogen or cyano;
M is hydrogen, lower alkyl, or alkali metal;

Z is CH—R$^9$ where R$^9$ is hydrogen, α-fluoro, or α-lower alkyl; and the dotted line between positions 1 and 2 represents the possibility of a single bond when Z is CH—R$^9$ and a double bond when Z is C—R$^9$; comprising the steps of (1) reacting a 17β-(1-ketoethy)-5-androsten-3-ol with pyridine and iodine to form a pyridinium iodide compound;

(2) reacting the pyridinium iodide compound with alkali metal methoxide in methanol to form a methyl-5-androsten-3-ol-17β-carboxylate;

(3) oxidizing the 5-androsten-3-ol to form methyl-4-androsten-3-one-17β-carboxylate; and (4) hydrolyzing the methyl-17β-carboxylate to the corresponding 17β-carboxylic acid.

2. The method of claim 1 wherein in the third step the oxidizing is carried out using aluminum isopropoxide and cyclohexanone.

3. The method of claim 1 wherein in the fourth step the hydrolyzing is carried out using potassium hydroxide in a mixture of methanol and water.

4. A method for preparing methyl 5-androsten-3-ol-17β-carboxylates having the formula:

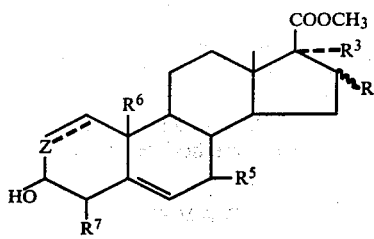

where
R$^3$, R$^4$, R$^5$, and R$^6$ are the same or different and are hydrogen or lower alkyl;
R$^7$ is hydrogen or cyano;
M is hydrogen, lower alkyl, or alkali metal;
Z is CH—R$^9$ where R$^9$ is hydrogen, α-fluoro, or α-lower alkyl; and the dotted line between positions 1 and 2 represents the possibility of a single bond when Z is CH—R$^9$ and a double bond when Z is C—R$^9$; comprising the step of reacting a compound of the formula:

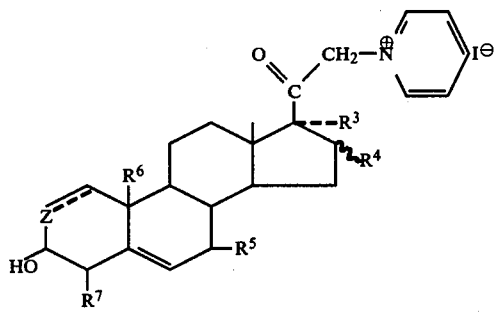

wherein R$^3$, R$^4$, R$^5$, R$^6$, R$^7$ and Z have the same meaning as above, with alkali metal methoxide in methanol.

* * * * *